(12) United States Patent
Chanduszko et al.

(10) Patent No.: US 8,348,945 B2
(45) Date of Patent: Jan. 8, 2013

(54) WELDING SYSTEMS USEFUL FOR CLOSURE OF CARDIAC OPENINGS

(75) Inventors: Andrzej J. Chanduszko, Chandler, AZ (US); David R. Widomski, Wakefield, MA (US); Carol A. Devellian, Topsfield, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 0 days.

(21) Appl. No.: 13/189,438

(22) Filed: Jul. 22, 2011

(65) Prior Publication Data

US 2011/0282345 A1    Nov. 17, 2011

Related U.S. Application Data

(62) Division of application No. 11/044,657, filed on Jan. 27, 2005, now Pat. No. 7,988,690.

(60) Provisional application No. 60/540,827, filed on Jan. 30, 2004, provisional application No. 60/540,821, filed on Jan. 30, 2004, provisional application No. 60/540,474, filed on Jan. 30, 2004.

(51) Int. Cl.
*A61B 18/14*    (2006.01)

(52) U.S. Cl. ............... 606/49; 606/216; 606/41
(58) Field of Classification Search ............... 606/41, 606/48–50, 213–216; 607/101, 102, 116, 607/122; 128/898
See application file for complete search history.

(56) References Cited

U.S. PATENT DOCUMENTS

| | | | |
|---|---|---|---|
| 7,165,552 B2 * | 1/2007 | Deem et al. ................. | 128/898 |
| 7,186,251 B2 * | 3/2007 | Malecki et al. ............. | 606/41 |
| 7,637,924 B2 * | 12/2009 | Gifford et al. .............. | 606/213 |
| 7,797,056 B2 * | 9/2010 | Forde et al. ................. | 607/116 |

* cited by examiner

*Primary Examiner* — Michael Peffley
(74) *Attorney, Agent, or Firm* — DLA Piper LLP (US)

(57) ABSTRACT

A welding element is provided for applying heat, chemicals, pressure, or any combination thereof to tissues inside a patient's body, e.g., a patent foramen ovale. In one aspect, the welding element is connected to a radio frequency energy source and includes an electrode and a locator. The locator facilitates positioning of the welding element and is capable of moving from an open position to a clamping position. In another aspect, a needle is provided for transseptal puncturing before the application of heat. In yet another aspect, the welding element is configured as a coil. The welding element can be made of Nitinol.

17 Claims, 17 Drawing Sheets

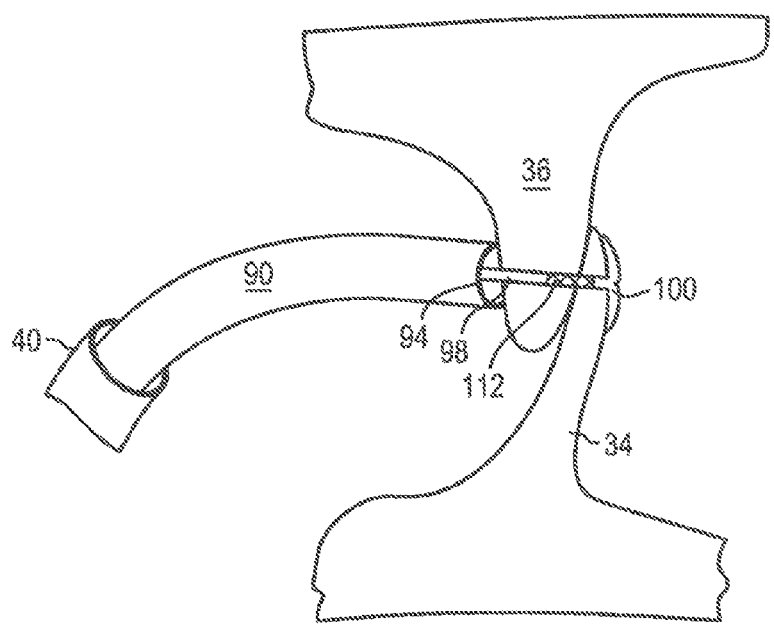
FIG. 17A
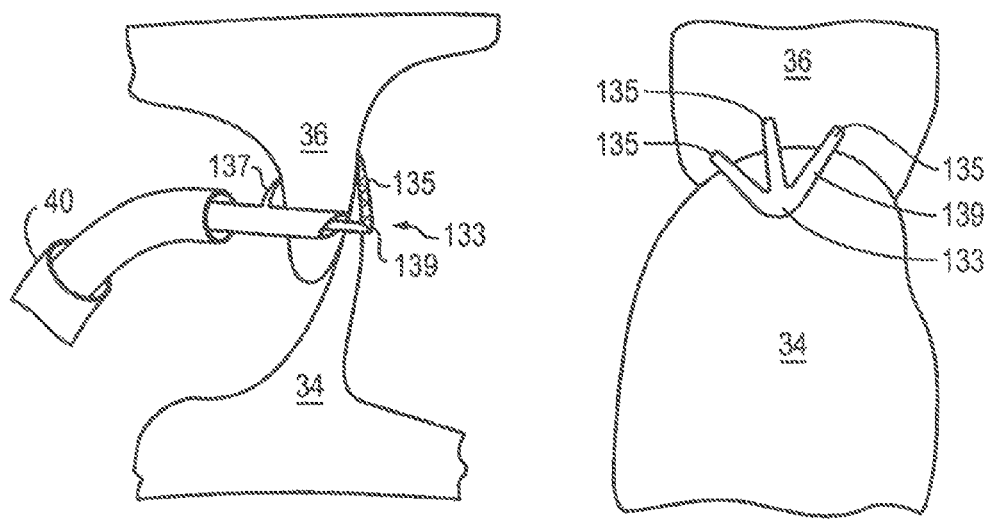
FIG. 17B
FIG. 17C

WELDING SYSTEMS USEFUL FOR CLOSURE OF CARDIAC OPENINGS

CROSS REFERENCE TO RELATED APPLICATIONS

This application is a divisional application of U.S. application Ser. No. 11/044,657 filed Jan. 27, 2005, now issued as U.S. Pat. No. 7,988,690; which claims the benefit under 35 USC §119(e) to U.S. Application Ser. No. 60/540,827 filed Jan. 30, 2004, U.S. Application Ser. No. 60/540,821 filed Jan. 30, 2004 and U.S. Application Ser. No. 60/540,474 filed Jan. 30, 2004. The disclosure of each of the prior applications is considered part of and is incorporated by reference in the disclosure of this application.

BACKGROUND OF THE INVENTION

1. Field of the Invention

The invention generally relates to devices, systems, and related methods for closing cardiac openings through tissue welding. An exemplary application of the invention can be found in closing a patent foramen ovale.

2. Background Information

The human heart is divided into four compartments or chambers. The left and right atria are located in the upper portion of the heart and the left and right ventricles are located in the lower portion of the heart. The left and right atria are separated from each other by a muscular wall, the intraatrial septum, while the ventricles are separated by the intraventricular septum.

Either congenitally or by acquisition, abnormal openings, holes, or shunts can occur between the chambers of the heart or the great vessels, causing blood to flow therethrough. Such deformities are usually congenital and originate during fetal life when the heart forms from a folded tube into a four chambered, two-unit system. The deformities result from the incomplete formation of the septum, or muscular wall, between the chambers of the heart and can cause significant problems.

One such deformity or defect, a patent foramen ovale, is a persistent, one-way, usually flap-like opening in the wall between the right atrium and left atrium of the heart. In the fetus, the foramen ovale serves as a conduit for right-to-left atrial shunting. After birth, with the establishment of pulmonary circulation, the increased left atrial blood flow and pressure results in functional closure of the foramen ovale. Normally, this is followed by anatomical closure of the two overlapping layers of tissue at the foramen ovale: the septum primum and the septum secundum. However, in certain individuals, a patent foramen ovale (PFO) persists. Depending on the method used to detect a PFO, an estimated 25 to 35% of adults have PFO.

Because the left atrial pressure is normally higher than right atrial pressure, the flap in people with a PFO typically stays closed. However, under certain conditions, right atrial pressure exceeds left atrial pressure, creating the possibility for right to left shunting that can allow blood clots to enter the systemic circulation. Consequentially, paradoxical embolism via a PFO is being considered in diagnosing causes for ischemic strokes, especially in young patients. Many studies have confirmed a strong association between the presence of a PFO and the risk for paradoxical embolism or stroke. In addition, there is good evidence that patients with PFO and paradoxical embolism are at increased risk for future, recurrent cerebrovascular events.

Patients suffering a stroke or transient ischemic attack (TIA) in the presence of a PFO and without another apparent cause for ischemic stroke are considered for prophylactic medical therapy to reduce the risk of a recurrent embolic event. These patients are commonly treated with oral anticoagulants which have the potential for adverse side effects, such as hemorrhage, hematoma, and adverse interactions with other drugs. In certain cases, such as when anticoagulation is contraindicated, surgery may be used to close a PFO. Under direct visualization, a surgeon can suture together the septum secundum and septum primum with a continuous stitch.

Nonsurgical (i.e., percutaneous) closure of patent PFO, as well as other cardiac openings such as atrial septal defects and ventricular septal defects, have become possible using a variety of mechanical closure devices. Currently available closure devices, however, are often complex to manufacture and require a technically complex implantation procedure. Because they are mostly designed to close septal defects, which are actual holes different from the flap-like anatomy of PFO, the existing devices lack more specific anatomic conformability for closing PFO and other similar cardiac openings.

Improved devices, systems, and related methods for closing cardiac openings, such as PFO, are, therefore, needed.

SUMMARY OF THE INVENTION

The present invention provides devices, systems, and related methods for welding tissues, i.e., fusing previously separate tissues together, at least temporarily, through heat, chemicals, e.g., collagen or fibrinogen, pressure, or combinations of the above inside a patient as exemplified by procedures for closing cardiac openings. In one aspect, devices of the invention are configured to apply heat and/or pressure to the target tissue such as tissues lining a cardiac opening. An embodiment of this aspect of the invention can be found in an intravascular catheter that has an elongated sheath and a welding element located in the sheath's bore. The welding element is also extendable out of one of two ends of the sheath for deployment. The welding element includes an electrode and a locator. The locator facilitates proper positioning of the welding element inside a vascular system, and is capable of moving from an open position to a clamping position. The locator may be attached to the distal end of the electrode at an angle relative to the longitudinal axis of the electrode. The angle can be acute, obtuse, or substantially perpendicular. The angle may decrease, thus, moving from the open position to the clamping position when connected to an energy source, e.g., a radio frequency energy source. Additionally, the locator may include a second electrode or a balloon. The welding element may move between a deployed configuration and a retracted configuration. The welding element may be operably attached to an elongated cable to help transition the welding element between the deployed configuration and the retracted configuration.

The electrode in the welding element may be flexible. The electrode may be less than 1 mm in diameter. At least part of the welding element, e.g., the electrode(s) and/or the locator, may be made at least in part of Nitinol. In one embodiment, the welding element generates a clamping force when the electrode is connected to an energy source. The welding element may be releasable. Additionally, the welding element may comprise three electrodes or may comprise a coil. The welding element may also be capable of releasing welding agents to facilitate tissue reparation, e.g., fibrinogen, collagen, and/or an adhesive. The intravascular catheter may also comprise a hollow needle disposed at a first end of the elongated sheath.

In another aspect of the invention, for treatment of an intracardiac site, the welding element includes a needle. Accordingly, an intravascular catheter that has an elongated catheter body, a hollow needle, a distal tissue anchor, and an electrode is provided. The needle may be used for transseptal puncturing. The catheter body has a proximal end and a distal end. The needle has a distal tip and a proximal end, and a bore extending from the distal tip towards the proximal end. The needle is disposed at the distal end of the catheter body. In one embodiment, the needle is at least about 7 mm long. The distal tissue anchor is deployable from the distal end of the catheter body, e.g., in the bore of the needle before being deployed. The distal tissue anchor may include a plurality of prongs. The electrode is disposed at the distal end of the catheter body and connectable to an energy source, e.g., a source of RF energy. The catheter may also be capable of releasing welding agents to facilitate tissue reparation, e.g., fibrinogen, collagen, and/or an adhesive.

The electrode may be located at various parts of the distal end of the catheter body. It may comprise at least a portion of a wire that slidingly deploys the distal tissue anchor from the bore of the needle. The electrode may also comprise at least a portion of the distal tissue anchor or the needle. The electrode may be made, at least partly, of Nitinol.

Further, a proximal anchor can be added to exert a force opposite the distal anchor. The proximal anchor may include a plurality of prongs, each prong measuring less than about 6 mm. In one embodiment, the intravascular catheter may further include a second electrode deployed proximal to the distal tissue anchor. The proximal tissue anchor may comprise at least a portion of the second electrode. The proximal tissue anchor may comprise the distal end of the catheter sheath.

In another aspect of the invention, the welding element is configured as a coil. Accordingly, an intravascular catheter that has a coil having an insulated portion and uninsulated portion is provided where the uninsulated portion includes an electrode connectable to an energy source. The energized electrode provides heat to an intracardiac site requiring treatment. The catheter may further include an elongated sheath with a proximal end, a distal end, and defines a bore, where the coil is extendable from inside the bore. In one embodiment, the coil has a first pitch and a different second pitch. In one embodiment, at least one of the first or second pitch decreases when the electrode is connected to an energy source, e.g., a RF energy source, thereby generating a clamping force. In another embodiment, both the first and second pitches decrease when the electrode is energized. In yet another embodiment, the coil is releasable from a distal end of the welding element, i.e., from the rest of the intravascular catheter.

In one embodiment, the first pitch of the coil measures between about 5 mm and about 10 mm, e.g., for securing a patient's septum secundum, and the second pitch measures less than about 1.5 mm, e.g., for securing a patient's septum primum. The coil may be made of a shape-memory material, e.g., Nitinol. The coil may also be capable of releasing welding agents, e.g., fibrinogen, collagen, and an adhesive.

In yet another aspect of the invention, a method for treating a patent foramen ovale in the heart of a patient is provided. The method includes introducing an intravascular catheter into a patient's heart. The catheter includes an elongated sheath and a welding element disposed within the sheath's bore. The welding element is extendable out of one end of the sheath's bore and includes an electrode and a locator. The welding element is extended between the patient's septum primum and septum secundum in the heart. The locator is transitioned between an open position and a clamping position to position the welding element such that it contacts both the patient's septum primum and septum secundum. Energy is then applied to the electrode to heat the patient's septum primum and septum secundum.

In another embodiment of a method for treating a patent foramen ovale in the heart of a patient according to the present invention, an intravascular catheter is introduced into the patient's heart, the catheter comprising a coil that includes an electrode. The coil is engaged with both the septum secundum and septum primum such that the electrode contacts both the septum secundum and septum primum. The electrode is connected to an energy source to heat both the septum secundum and septum primum. The method may include generating a clamping force in the coil when the electrode is energized to keep the septum secundum and septum primum in contact with each other during heating.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 17A is a schematic side view illustrating an alternative step following FIG. 14 where heat is applied through a portion of a cable that supports the distal anchor, according to an illustrative embodiment of the invention.

FIG. 17B is a schematic side view illustrating a method for using the embodiment depicted in FIG. 12B.

FIG. 17C is another side view normal to the view depicted in FIG. 17B, according to an illustrative embodiment of the invention.

DETAILED DESCRIPTION OF THE INVENTION

The present invention relates to devices, systems, and related methods for heating tissues inside a patient's body, e.g., for closing cardiac openings such as a PFO tunnel. A welding element is provided for applying heat and/or pressure to cardiac tissues. An exemplary application for the welding element is to fuse the septum primum to the septum secundum, thereby closing the PFO tunnel. In one aspect of the invention, a locator is provided for proper positioning of the welding element. In another aspect, a puncturing means is provided in the welding element. In yet another aspect of the invention, the welding element is shaped in a coil. Any of these and other aspects of the invention can be combined.

Figure 1A:
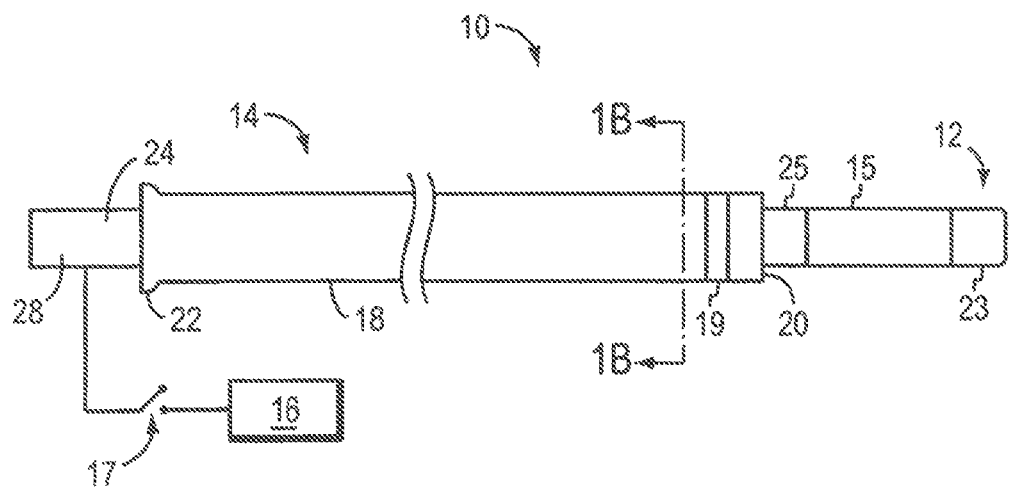
FIG. 1A is a schematic view of an intravascular catheter with a welding element according to an illustrative embodiment of the invention.

Referring to FIG. 1A, an exemplary percutaneous hansluminal system 10 can be used for closing a cardiac opening. The system 10 includes a welding element 12 at a distal end of a carrier or delivery device, such as any suitable type of catheter 14. For example, if the catheter 14 is to be used to access the heart from a femoral site, it will typically need a length between about 80 to about 140 cm. In one embodiment, the catheter 14 has an elongated sheath 18 with a distal end 20 and a proximal end 22. The sheath 18 may also include a radio-opaque marker 19, e.g., a metal ring, at a desired location on the catheter, e.g., the catheter distal end 20. The catheter 14 may include additional channels for optional functions, such as irrigating the welding site with a fluid, a drug solution or an agent. Such constructions are well known in the art of transluminal devices.

With continued reference to FIG. 1A, the welding element 12 is connectable to an energy source, e.g., a radio frequency (RF) source 16. A switch 17 maybe included to control the connection. Other energy sources include, and are not limited to, AC (other than RF) or DC electricity and so on. Heat at the welding element 12 can be generated through radio frequency or other means, e.g., resistance heating. The entirety or part(s) of the welding element 12 may generate heat, e.g., by acting as electrodes connected to a source of electric current. In one embodiment, at least part-of the welding element 12 is flexible or semi-flexible, i.e., can be bent or flexed without permanent damage that compromises its functionality (e.g., visible fracture). In a preferred embodiment, at least a portion, e.g., a body portion 15, of the welding element 12 can be bent into or assumes, e.g., upon heat activation, a configuration that conforms to the anatomical shape or contour of the PFO, such that the welding element 12 can contact both the septum primum and septum secundum at the same time. Such a configuration enables the application of heat and/or pressure to both the septum primum and septum secundum at the same time, and is advantageous in non-surgical treatment of PFO. In one embodiment, the welding element 12 is made of a shape-memory material such as Nitinol that assumes the desired configuration once connected to an energy source and reaches a certain temperature.

Still referring to FIG. 1 A, the welding element 12 may include one or more electrodes (not shown). In the embodiment where there is only one electrode in the welding element 1.2, a second reference electrode (ground) connected to the energy source may be placed on the patient's thighs or other suitable areas. Parts of the welding element 12 that will likely contact blood during its operation may be insulated. For example, a distal portion 23 of the welding element 12 may be insulated (not shown). There are a variety of ways to insulate an otherwise conductive body, e.g., with a non-conductive sleeve or coating, or embedding a non-conductive barrier between the insulated portion and the uninsulated portion. In other words, the insulated and uninsulated portions can be made essentially of the same material but somehow sectionalized to be selectively heat-conductive when the welding element 12 is energized. In one embodiment, a non-thrombogenic polymer half sleeve or foam coating is applied for insulation purposes.

Figure 1B:
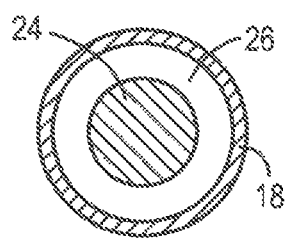
FIG. 1B is a cross-sectional view of the system of FIG. 1A along the line 1B-1B.

With reference to FIG. 1A, the welding element 12 is carried by an elongated cable 24 at its distal end 25. As best illustrated in FIG. 1B, the elongated cable 24 slidingly extends inside a bore 26 defined by the catheter sheath 18. The welding element 12 may stay inside the bore 26 until it has been delivered to the desired anatomical location, e.g., close to the septum secundum. In one embodiment, referring to FIG. 1A, the RF source 16 is connected to a proximal end 28 of the carrying cable 24 and RF energy is supplied through an electric cable (not shown) insulated inside the carrying cable 24 to the electrodes(s) at the cable distal end 25. Alternatively, there maybe other means and associated features for delivering and heating the welding element 12 as known to one skilled in the art of transluminal devices.

Figure 2A:
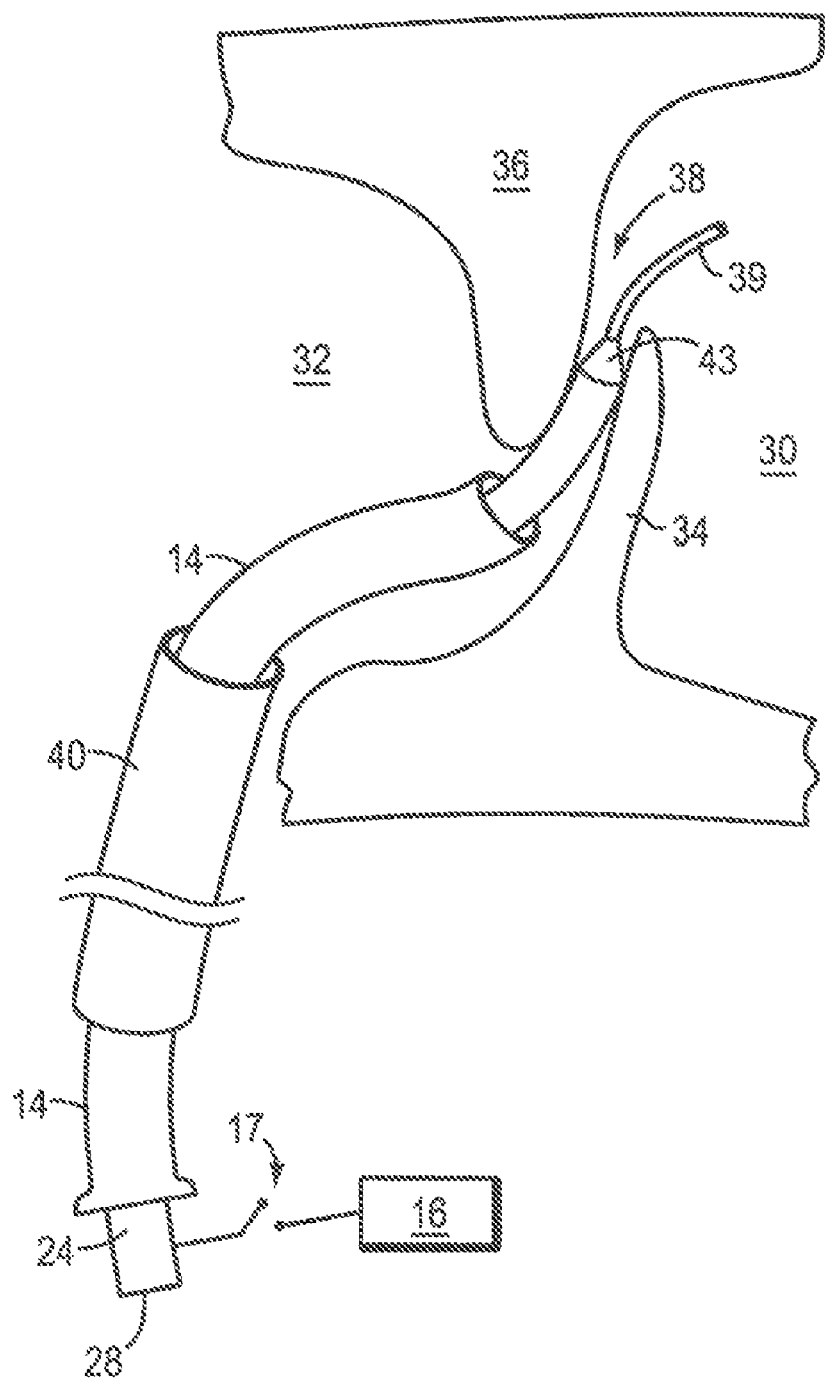
FIGS. 2A, 2B and 2C are schematic side views illustrating how the system of FIG. 1A is used to treat a patent foramen ovale according to an illustrative embodiment of the invention.
Figure 2B:
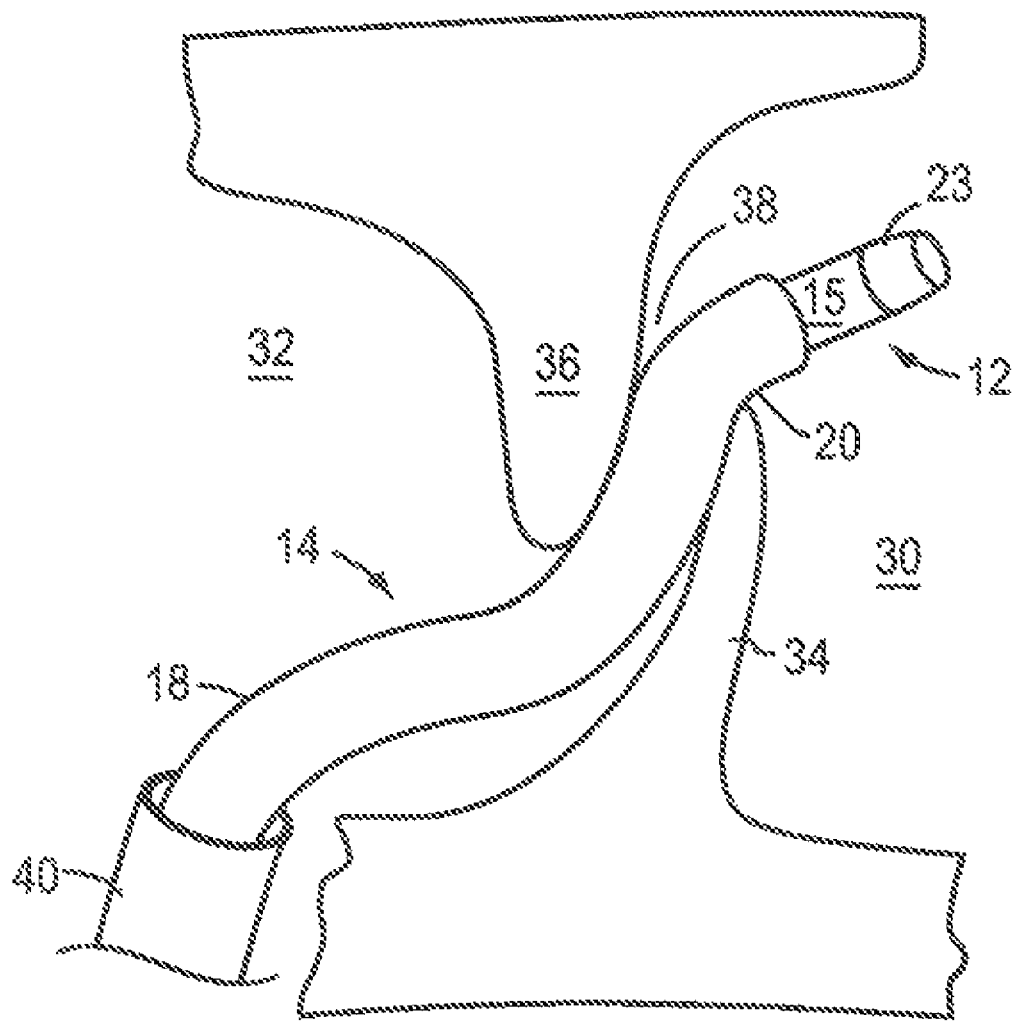
Figure 2C:
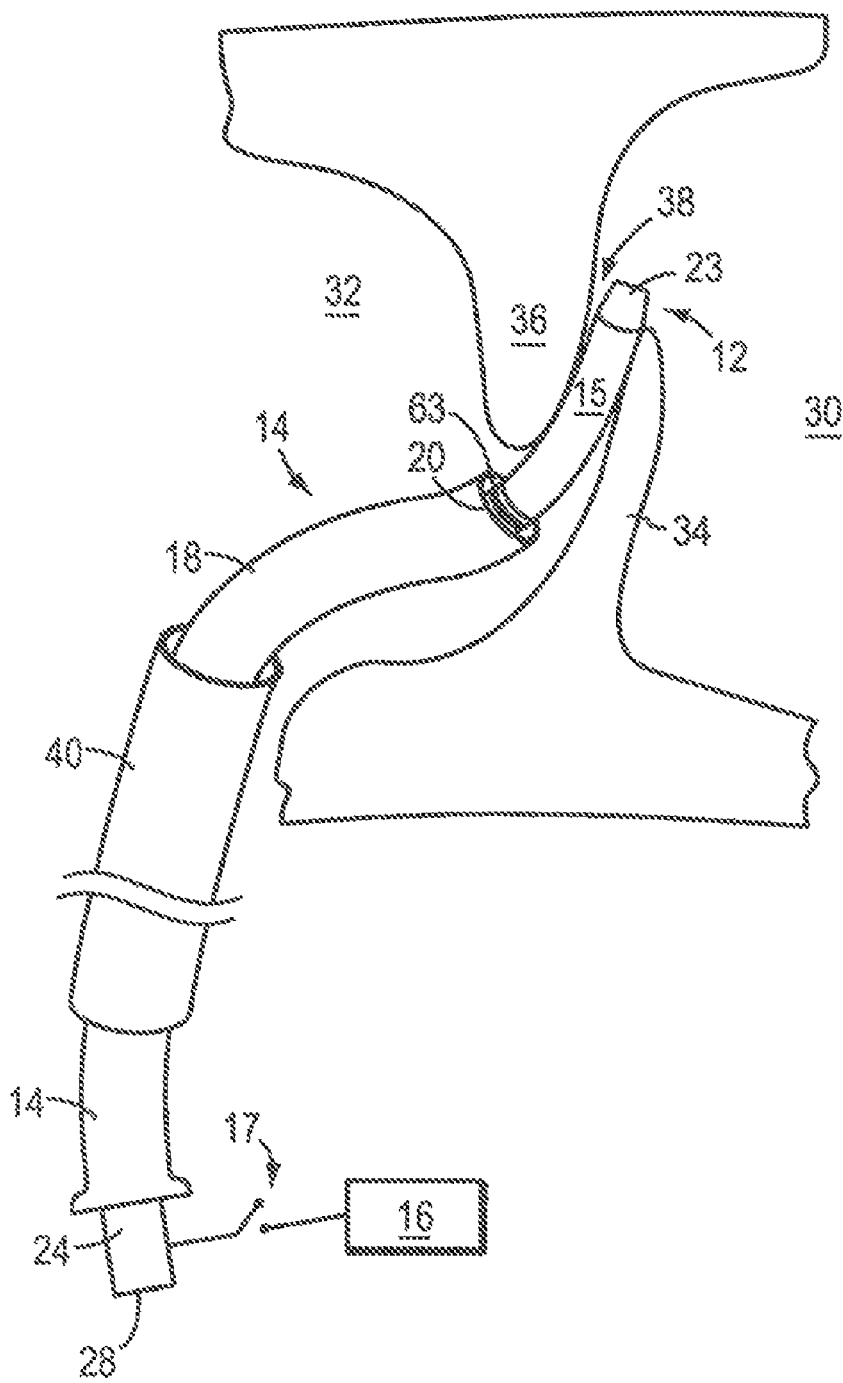

FIGS. 2A-2C depict how the device of the invention can be used to heat the tissue, e.g., to close a cardiac opening. In this example, the left atrium 30 and the right atrium 32 are shown to be separated by the septum primum 34 and septum secundum 36. A PFO 38 is shown as the space between the septum primum 34 and septum secundum 36. To access the PFO 38, the catheter 14 is advanced through the patient's skin into a blood vessel, e.g., through a standard femoral vein catheterization procedure. Other ways to access the heart, e.g., through the left atrium 30, may also be used. A guidewire 39 is typically used to facilitate the procedure.

Referring first to FIG. 2A, the guidewire 39 first accesses the right atrium 32 through the inferior vena cava 40, and progresses to the PFO 38 by travelling between the septum primum 34 and the septum secundum 36 until it accesses the left atrium 30. A dilator 43 may be passed over the guidewire 39 to temporarily dilate the PFO 38. The catheter 14 follows the same route and is threaded over the guidewire 39 to travel through the inferior vena cava 40, the PFO 38, until it reaches the left atrium 30 as shown in FIG. 2B.

Referring to FIG. 2B, the operator withdraws the guidewire 39 and, in its place, advances the carrying cable 24 through the bore of the catheter sheath 18 until the welding element 12 is delivered to the left atrium 30 and deployed outside the sheath distal end 20. Referring now to FIG. 2C, the operator then withdraws the catheter sheath 18 into the right atrium 32, and the welding element 12 into PFO 38 so that the welding body portion 15 is positioned in between the septum primum 34 and septum secundum 36. Depending on the structure of the welding element 12, its distal portion 23 may be exposed to blood in the left atrium 30. In that case, the distal portion 23 is preferably insulated so that it will not heat up blood during operation.

Referring to FIG. 2C, after confirming correct positioning of the welding element 12, e.g., under fluoroscopy or echocardiography or through the use of a locator described below, the operator switches on the switch 17 to connect the welding element 12 to the RF source 16. Consequently, heat is applied, through the electrode in the welding element 12, e.g., the welding body portion 15, to both septum primum 34 and septum secundum 36. Alternatively, the body portion 15 may make contact and apply heat to one of the septum primum 34 and septum secundum 36 before repositioning to make contact and apply heat to the other. The electrode, in this case, the welding body portion 15 causes the tissue to reach temperatures above 50° C., and in some cases, up to about 100° C. The high temperature causes tissue cells to die in the vicinity of the welding element 12. The heat along with the pressure differential between the atria 30 and 32 causes the septa to fuse and the PFO tunnel 38 to close. Welding agents and welding enhancing products, such as those encouraging or facilitating coagulation, tissue reparation, or wound healing, e.g., fibrinogen, or a bio-absorbable material such as collagen, can also be applied to the welding site, e.g., through a channel (not shown) inside the catheter 14 or through a coating on the welding element 12. The distal portion 23 and other parts of the welding element 12 that are exposed to blood are preferably insulated to prevent overheating the blood.

With continued reference to FIG. 2C, after a weld is created between the septum primum 34 and the septum secundum 36, the welding element 12 is pulled out of the tissue weld. And the operator removes the catheter 14 from the patient. Alternatively, if withdrawing the welding element 12 completely out of the weld will cause too much damages to the tissue, a portion of or the entire welding element 12 may be left in the tissue. In one preferred embodiment, for example, a portion of the welding element 12 is detachable from the carrying cable 24 at a detachment site 63. Such portion of the welding element 12 needs to be biocompatible to be left inside the patient.

Figure 3:
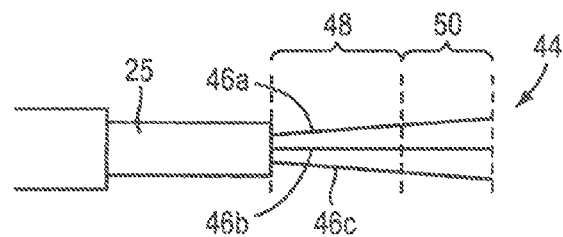
FIG. 3 is a side view of a welding element according to an illustrative embodiment of the invention.

FIG. 3 depicts an illustrative embodiment of the welding element according to the principle of the present invention. A welding element 44, disposed at the cable distal end 25, includes one or more electrodes, e.g., three electrodes 46a, 46b, and 46c. Each of the electrodes 46a, 46b, and 46c has a body portion 48 that is not insulated and capable of heating any contacting tissue. Preferably, each of the electrodes 46a, 46b, and 46c also includes an insulated portion 50, e.g., at their respective free end where they will likely contact blood during operation. The insulated portion 50 avoids heating up the blood in the heart compartments.

With continued reference to FIG. 3, the electrodes 46a, 46b, and 46c can be made of a variety of metals and alloys, such as steel, or copper. In one embodiment, they are made of Nitinol, which is a shape-memory alloy. In one embodiment, the electrodes are flexible or semi-flexible. The electrodes 46a, 46b, and 46c preferably assume a configuration compatible to the anatomical shape of the site of treatment, e.g., the PFO. In one embodiment, the electrodes 46a, 46b, and 46c are curved such that, when placed in the PFO, the electrode body portion 48 contacts both the septum primum and secundum at the same time. Alternatively, the electrodes 46a, 46b, and 46c can be bent or induced into such a configuration. In one embodiment, the electrodes 46a, 46b, and 46a are made of a shape-memory material such as Nitinol.

The electrodes 46a, 46b, and 46c can be made with a relatively thin profile. In one embodiment, the diameters of the electrodes 46a, 46b, and 46c are less than about 1 mm. With such small diameters, the electrodes 46a, 46b, and 46c can be pulled out of the weld without substantial damage to the weld.

Figure 4:
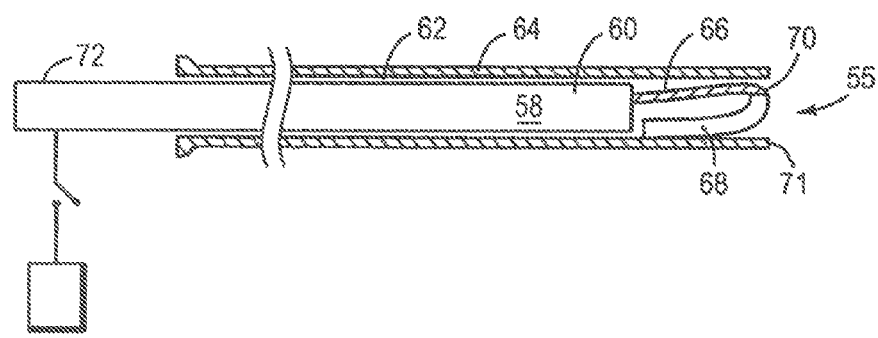
FIG. 4 is a partial cross-sectional view of an intravascular catheter with a distal locator collapsed inside the catheter sheath according to an illustrative embodiment of the invention.

FIGS. 4 through 9 depict another illustrative embodiment of the welding element and related method of use according to the principle of the invention. FIG. 4 depicts the embodiment in a collapsed or retracted configuration while FIGS. 5A and 5B depict the same embodiment in deployed configurations. Specifically, the embodiment is in an open position in FIG. 5A, and in a clamping position in FIG. 5B. FIGS. 6 through 9 depict steps in an illustrative method for using the embodiment depicted in FIGS. 4, 5A and 5B. Specifically, the method is used for closing the PFO but can be extended to other applications.

Referring to FIG. 4, an exemplary welding element 55 is joined to a distal end 60 of an elongated carrying cable 58. The carrying cable 58 slidingly extends inside a bore 62 defined by a catheter sheath 64. The welding element 55 includes at least two portions: a body portion 66 and a locator 68. In one embodiment, the locator 68 is joined to the body portion 66 at its distal end 70. In another embodiment (not shown), the locator 68 is joined to the proximal end of the welding body portion 66. The locator 68 may be shaped as one or more rods, disks, or any other objects that facilitate the proper positioning of the welding element 55. The locator 68 may include an inflatable portion such as a balloon (not shown).

Still referring to FIG. 4, before deployment, the welding element 55 is collapsed such that its body portion 66 and the locator 68 are folded together to be substantially inside a distal end 71 of the sheath bore 62. Now referring to FIG. 5A, after placing the sheath distal end 71 at the desired location inside the body, e.g., in the left atrium, the operator can deploy the welding element 55, e.g., by pushing the cable proximal end 72 in the distal direction so that the welding element 55 extends outside of the sheath distal end 71. When the operator pulls the welding element 55 back toward the sheath 64, the locator 68 is forced by the sheath distal end 71 to straighten out and to generally align with the longitudinal axis of the welding body portion 66, similar to the configuration shown in FIG. 9. The operator can subsequently withdraw the straightened welding element 55 into the sheath bore 62.

Figure 5A:
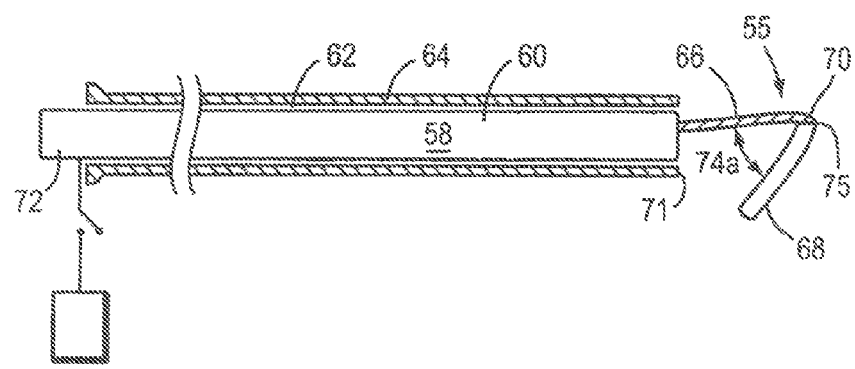
FIG. 5A is a partial cross-sectional view of the catheter of FIG. 4 with the distal locator deployed outside the catheter sheath at an open position, according to an illustrative embodiment of the invention.

As depicted in FIG. 5A, once outside the distal end 71 of the sheath 64, the welding element 55 opens up into its deployed configuration. In one embodiment, the locator 68 pivots away from the welding body portion 66 when deployed. A variety of mechanisms can be used to effect the pivot, for example, by having a spring, coil, or shape-memory material at the juncture between the welding body portion 66 and the locator 68. The welding body portion 66 may include one or more electrodes for generating heat. For example, the welding body portion 66 can be made of a metal or metal alloy such as Nitinol. The locator 68 can be an integral extension of the welding body portion 66 that is insulated. For example, the locator 68 may be made with or coated with a non-conductive material, e.g., a polymeric material. In one embodiment, both the welding body portion 66 and the core of the locator 68 are one piece of Nitinol, which tends to assume a pre-selected configuration, e.g., a hook, that is advantageous for an intended function once it reaches a temperature range such as from the room temperature to the body temperature, e.g., from about 25° C. to about 35° C.

Alternatively, the locator 68 and the welding body portion 66 can be separately manufactured and then joined together. Additionally, the locator 68 may include an electrode 69 connected to an energy source, e.g., and RF energy source. The electrode 69 may facilitate the locator 68 to change shape and to assume a pre-selected configuration or position. The electrode 69 may also aid in the welding function of the devise. For example, the electrode 69 may work in concert with another electrode in the welding body portion 66 to heat the tissue in between the electrodes. Alternatively, the electrode 69 may function as the sole electrode in the welding element 55.

Still referring to FIG. 5A, in the deployed configuration, the locator 68 initially forms, in an open position, an angle 74a with the longitudinal axis of the welding body portion 66. Such a hooked configuration allows the operator to retain the septum primum inside the hook, and therefore be sure of the position of the welding element 55 before turning on the heat. In that sense, the locator 68 serves as a positional marker useful for avoiding heating an unintended target. The open angle 74a can be obtuse, substantially perpendicular or acute, i.e., the open angle 74a is in the range of 0 to 180 degrees, preferably 45-90 degrees. In one embodiment, the open angle 74a is selected such that the deployed welding element 55 fits snugly over the tip of the septum primum 34.

Figure 5B:
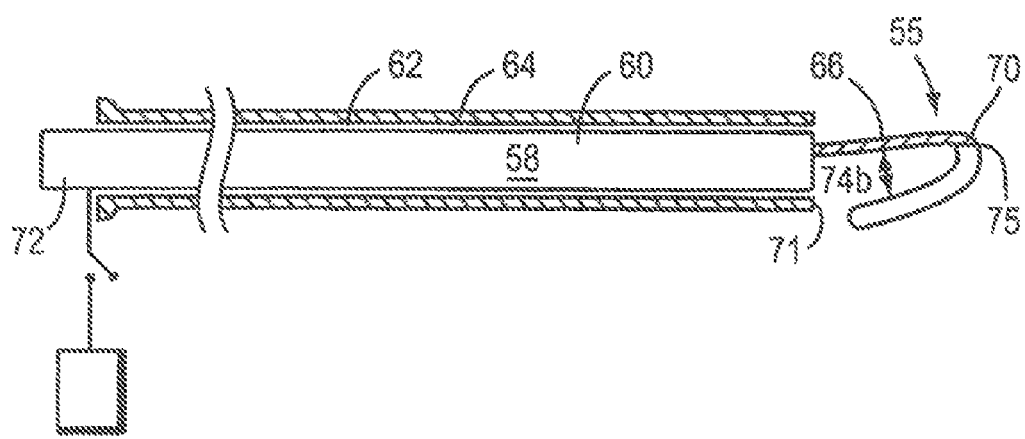
FIG. 5B is a partial cross-sectional view of the catheter of FIG. 4 with the distal locator deployed outside the catheter sheath at a clamping position, according to an illustrative embodiment of the invention.

Referring now to FIG. 5B, in one embodiment, at least the joint 75 between the welding body portion 66 and the locator 68 is made of a shape-memory material, e.g., Nitinol. With shape memory materials, in a clamping position, a clamping angle 74b between the locator 68 and the longitudinal axis of the welding body portion 66 gets narrower as the temperature changes to generate a clamping force against any tissue between the locator 68 and the welding body portion 66. One way to facilitate switching the locator 68 from the open position to the clamping position is to position the heat-generating electrode close to the joint 75, or making the joint 75 part of the electrode, so that its shape-memory material is heated up quickly.

Figure 6:
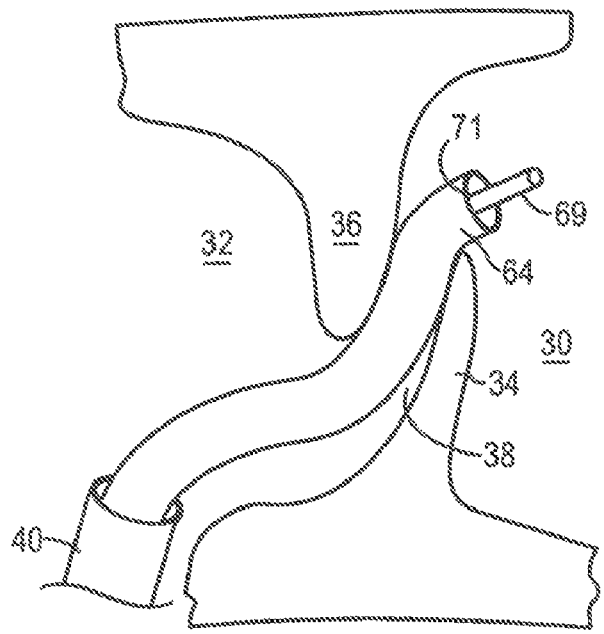
FIG. 6 is a schematic side view illustrating a PFO closure procedure using the catheter of FIGS. 4 and 5 where the catheter sheath is being pushed through the PFO tunnel to access the left atrium with its distal portion, according to an illustrative embodiment of the invention.

Referring specifically to FIG. 6, in an illustrative method for closing a PFO tunnel 38 using the embodiment described in FIGS. 4, 5A and 5B, the distal portion of the catheter sheath 64 is passed over a guidewire 69 and advanced through the inferior vena cava 40, the PFO 38, until its distal end 71 reaches the left atrium 30, in a way similar to what is described in connection with FIG. 2A. Then the guidewire 69 is withdrawn from the bore of the catheter sheath 64 and the welding element 55 is advanced, through its carrying cable 58, in the catheter bore 62 (FIG. 4) to the sheath distal end 71.

Figure 7:
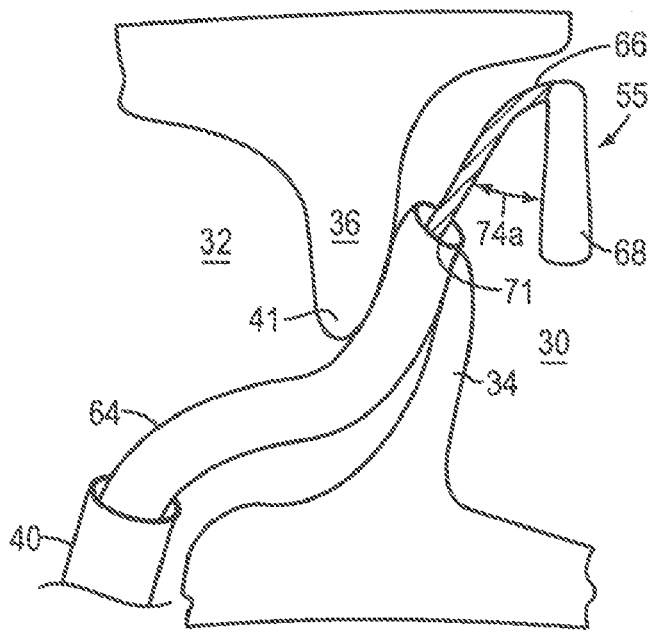
FIG. 7 is a schematic side view illustrating a step following FIG. 6 where the locator of the catheter is fully deployed, according to an illustrative embodiment of the invention.
Figure 8:
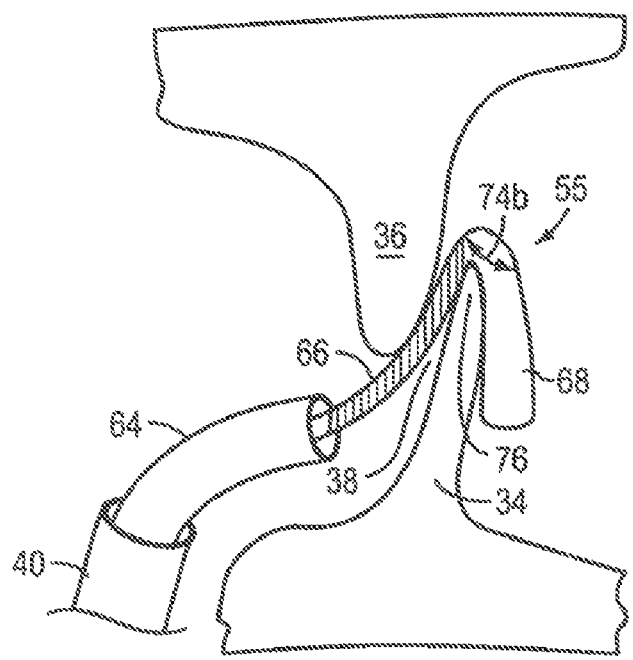
FIG. 8 is a schematic side view illustrating a step following FIG. 7 where the locator rests against the tip of the septum primum, according to an illustrative embodiment of the invention.

Referring to FIG. 7, once the welding element 55 reaches the left atrium 30, the operator advances it out of the sheath distal end 71 to deploy the welding element 55. Consequently, the locator 68 opens to its fully deployed configuration depicted previously in FIG. 5A, pivoted away from the welding body portion 66 at the open angle 74a. Referring now to FIG. 8, the operator then pulls the deployed welding element 55 toward the septum primum 34 until he or she senses resistance in movement, which indicates that the welding element 55 is resting against the tip portion 76 of the septum primum 34. Other configurations of the welding element 55 that facilitates the proper positioning of the welding body portion 66 in the PFO tunnel 38 between the septum primum 34 and the septum secundum 36 are also contemplated by the present invention. After the operator visually confirms the proper positioning, heat is applied through the welding element as described earlier, and the clamping angle 74b gets narrower, generating a clamping force. In a preferred embodiment, the core of substantially the entire welding element 55 is made of a shape memory material, e.g., Nitinol. The clamp force works in addition to the existing pressure differential between the atria to force the septum primum 34 and the septum secundum 36 against each other during and after the welding.

Figure 9:
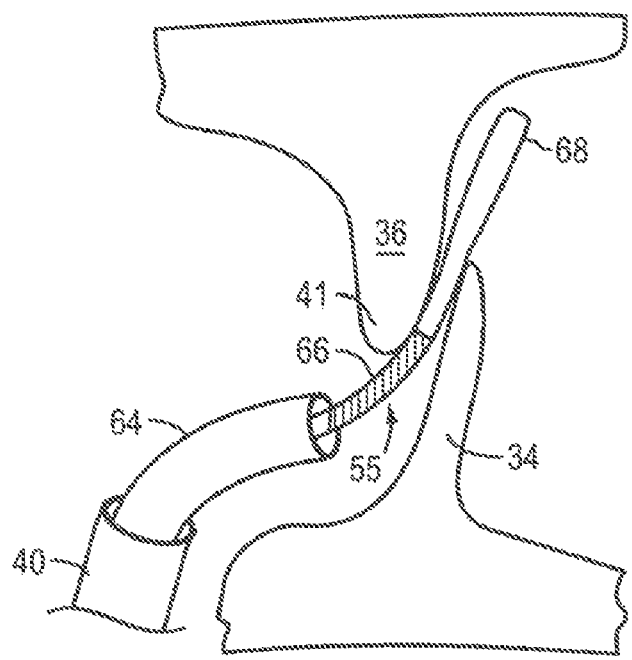
FIG. 9 is a schematic side view illustrating a step following FIG. 8 where the catheter is being withdrawn from the heart, according to an illustrative embodiment of the invention.

Referring to FIG. 9, after welding, the operator disconnects the electricity from the welding element 55, which reduces its clamping force. The operator can simply pull the welding element 55, e.g., by pulling its carrying cable 58 (FIG. 4), in the proximal direction to straighten out the welding element 55, as illustrated here, before pulling it out of the heart tissues.

Figure 10A:
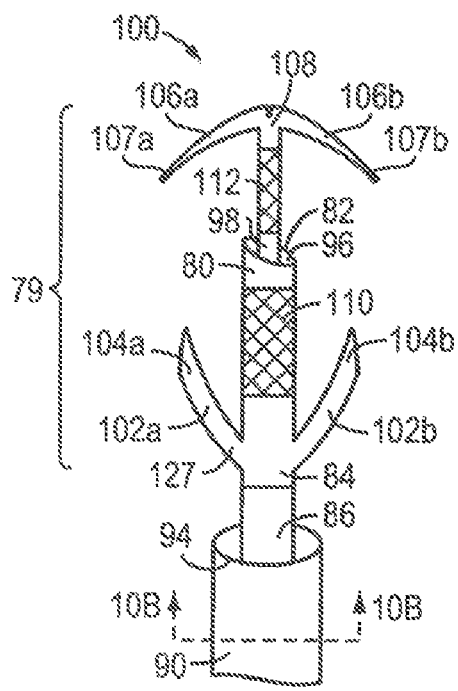
FIG. 10A is a side view of a welding element with a needle in a fully deployed state, according to an illustrative embodiment of the invention.

According to another aspect of the invention, some embodiments of the invention include a puncturing structure, e.g., a needle. The puncturing structure is useful in a variety of applications, e.g., transseptal puncturing. Referring to FIG. 10A, in an illustrative embodiment, a welding element 79 includes a hollow needle 80 that has a sharp distal tip 82, an opposite, proximal portion 84, and a bore 96 (best illustrated in FIG. 10B) extending from the distal tip 82 towards the proximal portion 84. In this particular embodiment, the needle distal tip 82 is beveled, but other shapes useful for puncturing tissue are also contemplated by the present invention. The needle proximal portion 84 is joined to a needle-carrying cable 86 that slidingly extends inside a bore 88 defined by a catheter sheath 90. By moving the needle-carrying cable 86, the operator can slide the needle 80 in and out of a distal end 94 of the catheter sheath 90 between a deployed configuration illustrated in FIG. 10A and a retracted configuration illustrated in FIG. 10C.

Still referring to FIG. 10A, an optional proximal anchor or locator 127 is attached to the needle 80. The proximal anchor 127 facilitates the proper positioning of the welding element 79. The proximal anchor 127 may have one or more proximal anchor prongs 102*a* and 102*b*. The free ends 104*a* and 104*b* of the proximal anchor prongs 102*a* and 102*b*, respectively, extend generally away from the proximal portion 84 of the needle 80 in the distal direction, i.e., toward the needle distal tip 82. The distal tips 104*a* and 104*b* of the proximal anchor prongs 102*a* and 102*b*, respectively, maybe sharp or blunt. The proximal anchor 127 may assume a variety of shapes, e.g., a stop ring (not shown), that assist in anchoring the needle 80 against a target tissue. In the embodiment illustrated in FIG. 10A, the proximal anchor 127 has proximal anchor prongs 102*a* and 102*b* which resemble prongs of a fork. More generally, the proximal anchor 127 may serve to immobilize the entirety, or part, of the welding element 79. In that sense, the proximal anchor 127 may serve the function akin to the locator 68 described above in other embodiments and help to facilitate the proper positioning of the welding element 79, for example, by acting as a proximal stopper against further advance of the needle 80. The needle 80 and the proximal anchor 127 may be manufactured as an integral piece and made of the same material such as a metal or metal alloy, e.g., Nitinol, or separately.

Figure 10B:
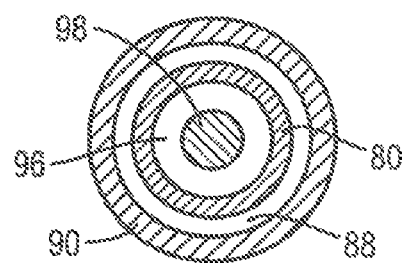
FIG. 10B is a cross-sectional view of the welding element of FIG. 10A taken along the line 10B-10B.
Figure 10C:
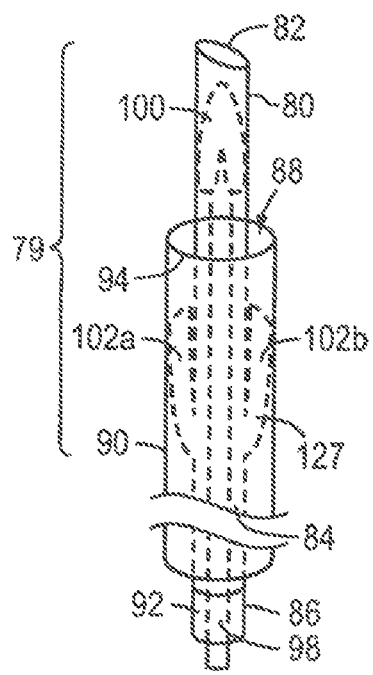
FIGS. 10C and 10D are perspective side views of the welding element of FIG. 10A in retracted states, according to an illustrative embodiment of the invention.

Referring briefly to FIG. 10C, to retract the proximal prong 127 into the catheter sheath 90, the operator may force the proximal anchor prongs 102*a* and 102*b* against the sheath distal end 94 into a collapsed or otherwise compact configuration as he pulls the needle 80, through the needle-carrying cable 86, into the catheter sheath bore 88.

Referring back to FIG. 10A, a central cable 98, carrying a distal anchor or locator 100 is slideably positioned within the needle bore 96. The spatial relationship between the catheter sheath 90, the needle 80, and the central cable 98 is illustrated in FIG. 10B. The distal anchor 100 also can switch between a deployed configuration illustrated in FIG. 10A and a retracted or collapsed configuration illustrated in FIGS. 10C and 10D. The distal anchor 100 may assume any of many desired configurations and shapes that facilitate anchoring the needle 80 against the target tissue. The distal anchor 100 serves to immobilize the entirety, or part, of the welding element 79. The distal anchor 100 may serve a function akin to the locator 68 described above in other embodiments and help to facilitate the proper positioning of the welding element 79, for example, by acting as a distal stopper against further advance of the needle 80. In one embodiment, the distal anchor 100 can resemble the locator 68 with the ability to move from an open position to a clamping position, generating a clamping force.

Still referring to FIG. 10A, in the illustrated embodiment, the distal anchor 100 includes one or more prongs 106*a* and 106*b* that are joined to a distal end 108 of the central cable 98. The prong tips 107*a* and 107*b* both pivot away from the central cable 98 in the deployed configuration through a spring, a coil, a shape-memory material, or other mechanism known to one skilled in the art. In one embodiment, the prongs 106*a* and 106*b* both curve backward in the deployed configuration, and the prong tips 107*a* and 107*b* are sharp for engaging tissue. The distal anchor 100 may be made of any suitable material such as a metal or metal alloy, e.g., Nitinol.

Figure 10D:
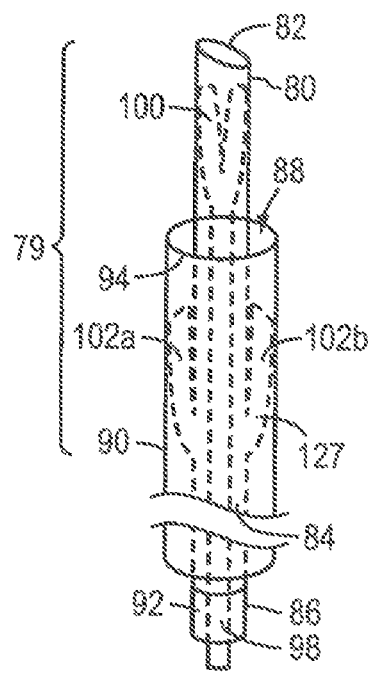

Referring to FIG. 10C, to deploy the distal anchor 100 from the retracted configuration, the operator pushes the central cable 98 in the distal direction to extend the distal anchor 100 out of the needle tip 82, which then expands into its deployed configuration depicted in FIG. 10A. Referring to FIG. 10D, to retract the distal anchor 100 back into the needle 80, the operator simply pulls the central cable 98 in the proximal direction while holding the needle-carrying cable 86 fast. The operator can force the prongs 106*a* and 106*b* to bend forward against the needle distal tip 82 in order to collapse them into the needle 80.

Referring back to FIG. 10A, the welding element 79 includes at least one electrode for applying heat to the target anatomical structure. In one embodiment, the entirety or part of the needle 80, e.g., an exposed middle portion 110 (with the rest of the needle 80 insulated), serves as an electrode. In another embodiment, an exposed portion 112 of the central cable 98 (with the rest of the central cable 98 insulated), serves as an electrode. In yet another embodiment, the entirety or part of the distal anchor 100 and/or the proximal anchor 127 serves as the electrodes. The proximal anchor 127 can also be used as a second electrode, so that electric current, e.g., AC, travels between the distal anchor 100 and the proximal anchor 127. Surfaces of the distal anchor 100 and proximal anchor 127 that will contact blood can be insulated through the application of a non-conductive, non-thrombogenic coating or sleeve (not shown), e.g., a polymeric half sleeve or a foam. Where the welding element 79 has only one electrode, a second reference electrode may be placed elsewhere on the patient body.

Figure 10E:
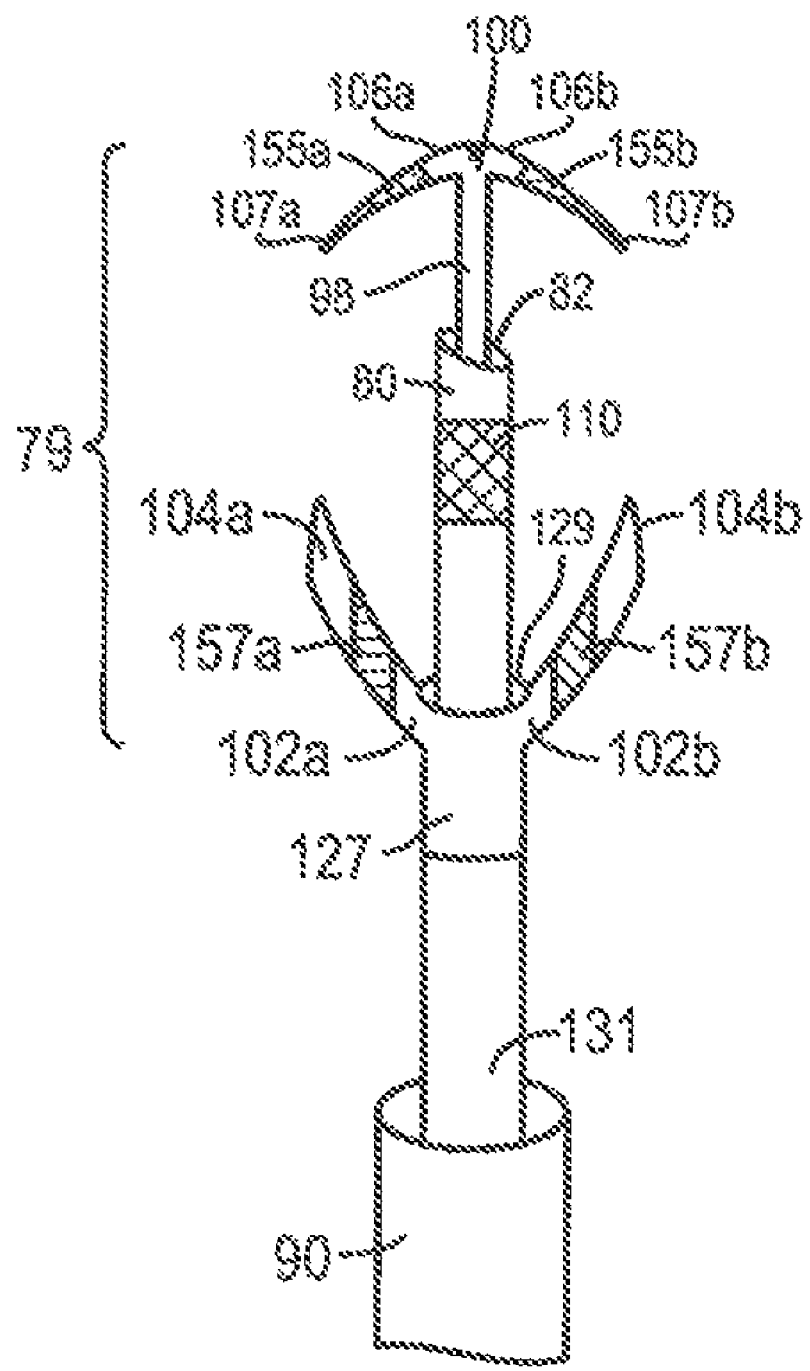
FIG. 10E is a side view of an alternative embodiment of FIG. 10A where the needle is separate from the proximal anchor.

Referring now to FIG. 10E, in an alternative embodiment of the invention, the distal anchor 100 may have electrodes 155*a* and 155*b* on the distal anchor prongs 106*a* and 106*b*, respectively. The proximal anchor prongs 102*a* and 102*b* may also have electrodes 157*a* and 157*b*, respectively, so that electric current, e.g., alternating current (AC), travels between the distal anchor electrodes (155*a* and 155*b*) and the proximal anchor electrodes (157*a* and 157*b*). In another embodiment, electric current can travel between the proximal electrodes (157*a* and 157*b*) and an electrode 110 on the needle 80. In another embodiment, electric current can travel between the distal anchor electrodes (155*a* and 155*b*) and the electrode 110 on the needle 80. In yet another embodiment, only a single electrode, for example, any of the electrodes 155*a*, 155*b*, 157*a*, 157*b*, or 110, is used.

Still referring to FIG. 10E, in the illustrated embodiment, the needle 80 is manufactured separately from the proximal anchor 127 such that the needle 80 and proximal anchor 127 can slide independent of each other. The proximal anchor 127 is joined to a second carrying cable 131. The needle 80 is slidingly disposed within a bore 129 in the proximal anchor 127. This alternative embodiment may include other features described in connection with other embodiments.

Figure 11:
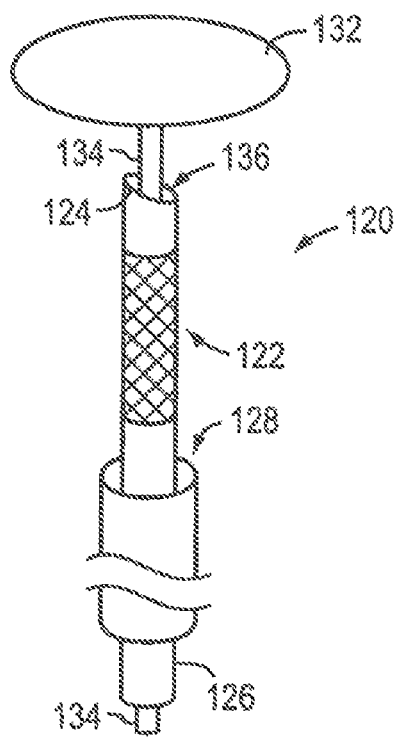
FIG. 11 is a side view of an embodiment of the welding element with a needle in a deployed state, according to the invention.

Referring to FIG. 11 in one embodiment of the invention, a welding element 120 includes a hollow needle 122 similar to the needle 80 described above, and parts of the welding element 120 also move between deployed and retracted configurations by virtue of axial movement of a needle-carrying cable 126 and a central cable 134. The needle 122, which has a sharp distal tip 124, is joined to the needle carrying cable 126 and therefore slidingly extends inside a bore 128 defined by a catheter sheath 130. A distal anchor 132, disposed at a distal end of the central cable 134, slidingly extends inside a needle bore 136 and is depicted in its deployed configuration in FIG. 12A. In the depicted embodiment, the distal anchor 132 assumes a largely planar and round surface.

Figure 12A:
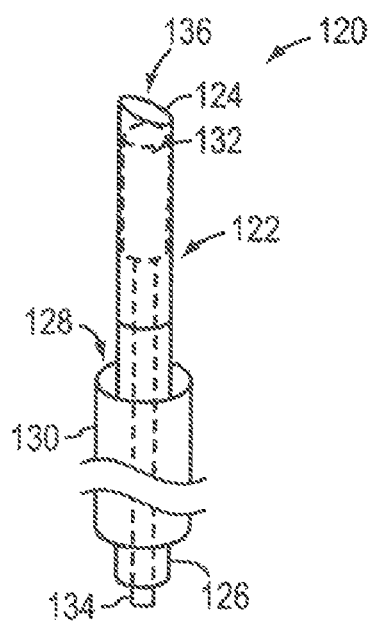
FIGS. 12A and 12B are perspective side views of the welding element of FIG. 11 where the distal locator is in retracted states, according to an illustrative embodiment of the invention.
Figure 12B:
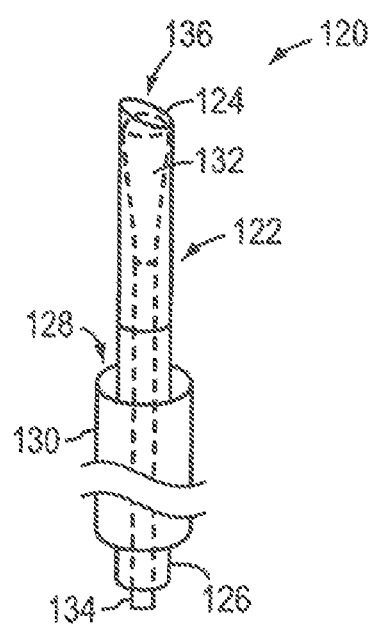

Referring to FIGS. 12A and 12B, the distal anchor 132 of welding element 120 in the embodiment depicted in FIG. 11 can assume a collapsed or otherwise compact configuration inside the needle bore 136.

Specifically Referring to FIG. 12 A, to deploy the distal anchor 132 from its retracted configuration, the operator pushes the central cable 134 to force the distal anchor 132 out of the needle distal tip 124, and the distal anchor 132 expands into its deployed configuration illustrated in FIG. 11. Referring now to FIG. 12B, to retract the distal anchor 132, the operator pulls the central cable 134 away from needle tip 124 while holding the needle carrying-cable 126 fast. The operator can force the planar surface of the distal anchor 132 to flip against the needle distal tip 124 in order to collapse into the needle. One or more proximal anchor or locator (not shown) may be optionally attached to a portion of the needle 122. The electrode(s) of the welding element 120 may be an exposed portion 138 of the needle 122, or the distal anchor, or the proximal anchor or a combination thereof.

Figure 13:
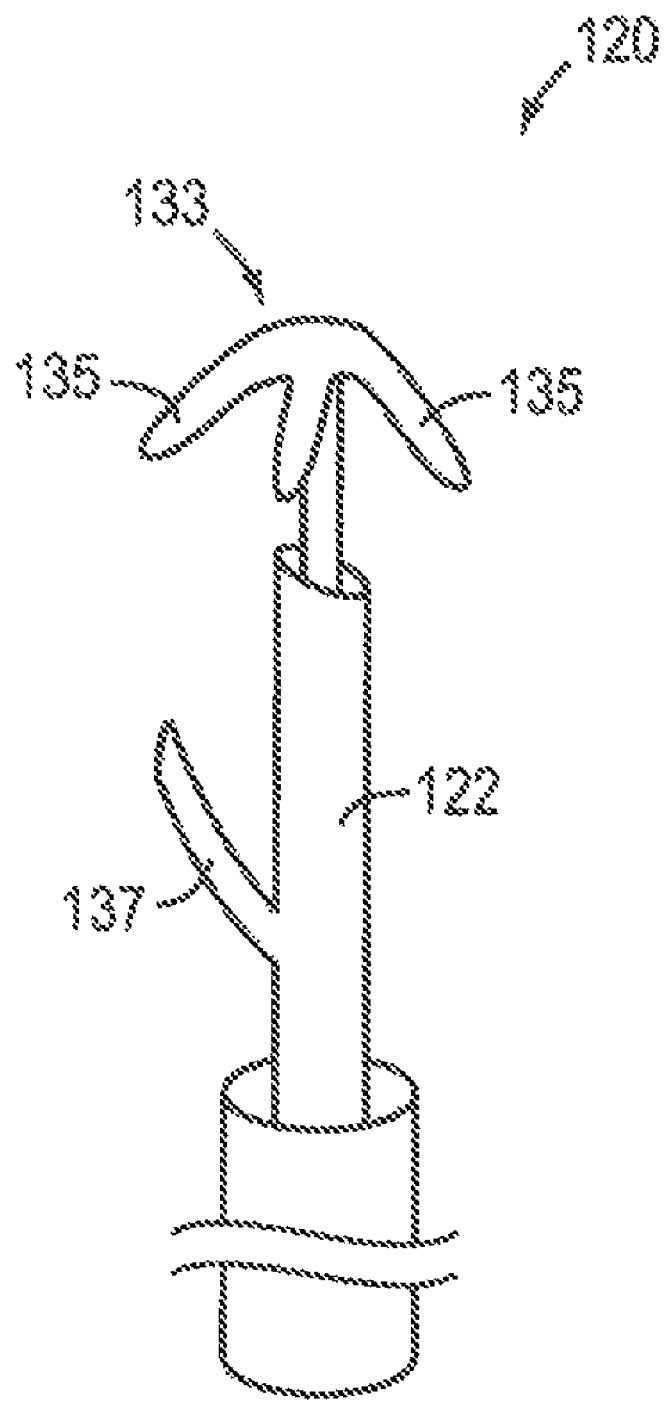
FIG. 13 is a side view of an embodiment of the welding element where the distal locator resembles a fork, according to the invention.
Figure 14:
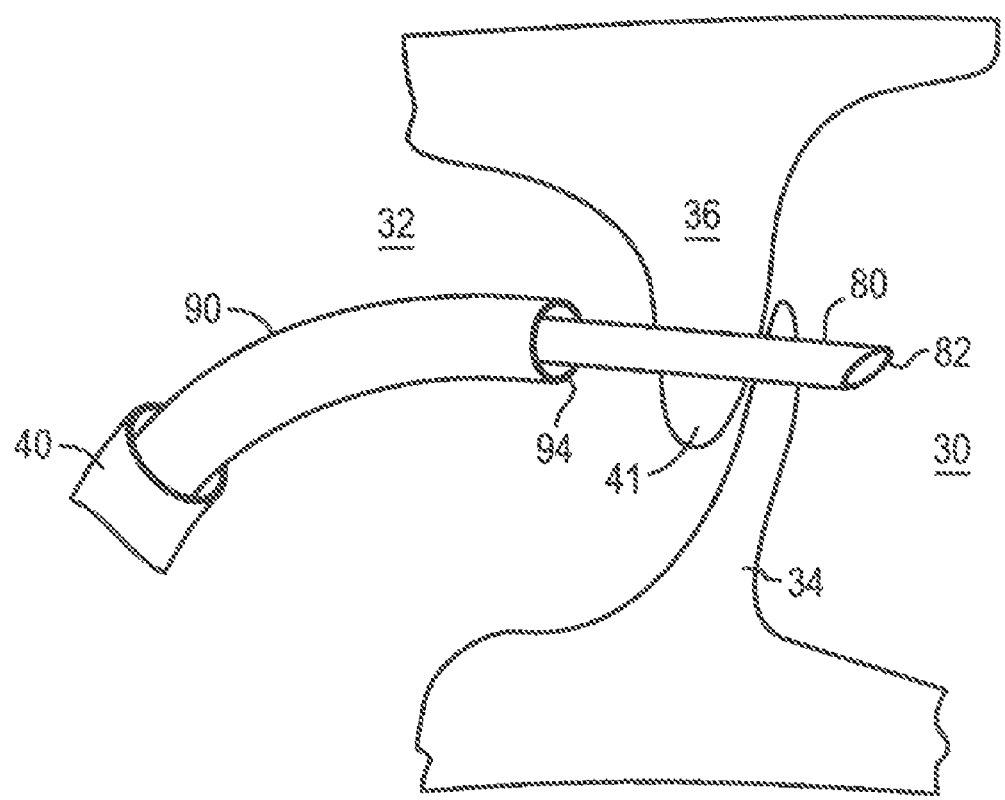
FIG. 14 is a schematic side view illustrating a PFO closure procedure using the catheter depicted in FIGS. 10A-10D where the needle penetrates both the septa secundum and primum, according to an illustrative embodiment of the invention.

Referring to FIG. 13, in another embodiment of the invention, a distal anchor 133 includes prongs 135 arranged like a fork. An optional proximal anchor 137 is associated with the needle 122 in a manner similar to that described above in connection with FIG. 10A.

FIGS. 14 through 17C depict steps in an exemplary method using any embodiment of the invention with a puncturing structure to close a cardiac opening, e.g., a PFO tunnel. Using the embodiment depicted in FIG. 10A as an example and referring first to FIG. 14, the operator accesses the heart as described previously, e.g., through the inferior vena cava 40 to the right atrium 32 with the welding element 79 (FIG. 10G) retracted inside the catheter sheath 90. Once the operator confirms, e.g., through real time 3D echocardiography, that the catheter distal end 94 reaches the septum secundum 36, he can deploy the needle 80 by sliding it out of the catheter distal end 94 into the septum secundum 36, preferably into the secundum tip portion 41. The average thickness of septum secundum 36 is about 6 mm to about 10 mm, and about 1 mm for septum primum 34. In a preferred embodiment, the needle 80 is from about 6 mm to about 15 mm so that its distal tip 82 not only penetrates the septum secundum 36 but also the septum primum 34.

Figure 15:
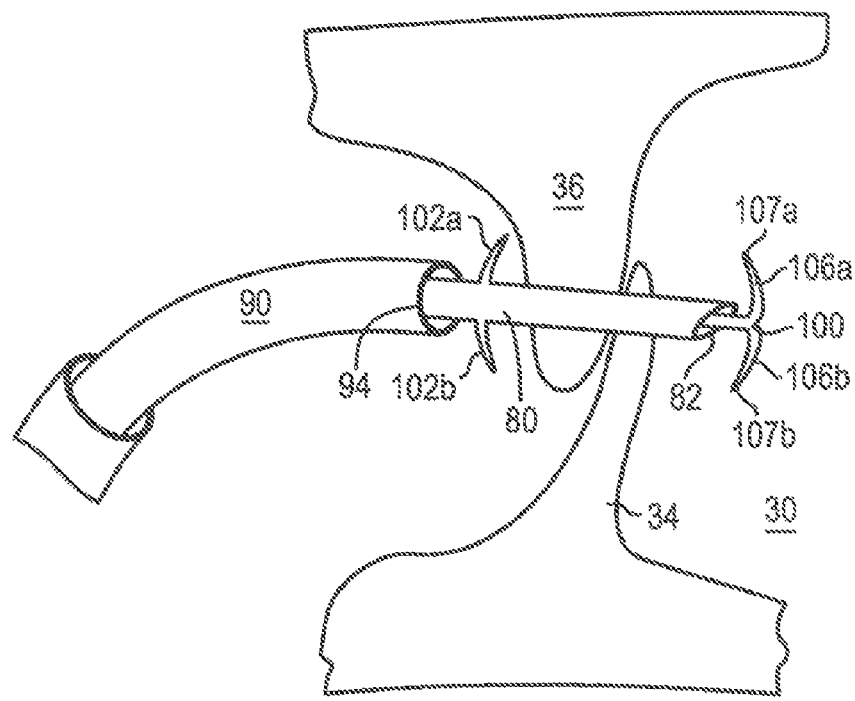
FIG. 15 is a schematic side view illustrating a step following FIG. 14 where both the distal anchor and the proximal anchors are deployed, according to an illustrative embodiment of the invention.

Referring to FIG. 15, the operator slides the distal anchor 100 out of the needle distal tip 82 and the distal anchor 100 expands into its deployed configuration with prongs 106a and 106b curving backward. The operator can then extend the needle 80 further out of the catheter distal end 94 so that the proximal anchor prongs 102a and 102b are out of the catheter sheath 90 and expand into the deployed configuration. The proximal anchor prongs 102a and 102b engage the septum secundum 36 with their fork-like configuration.

Figure 16:
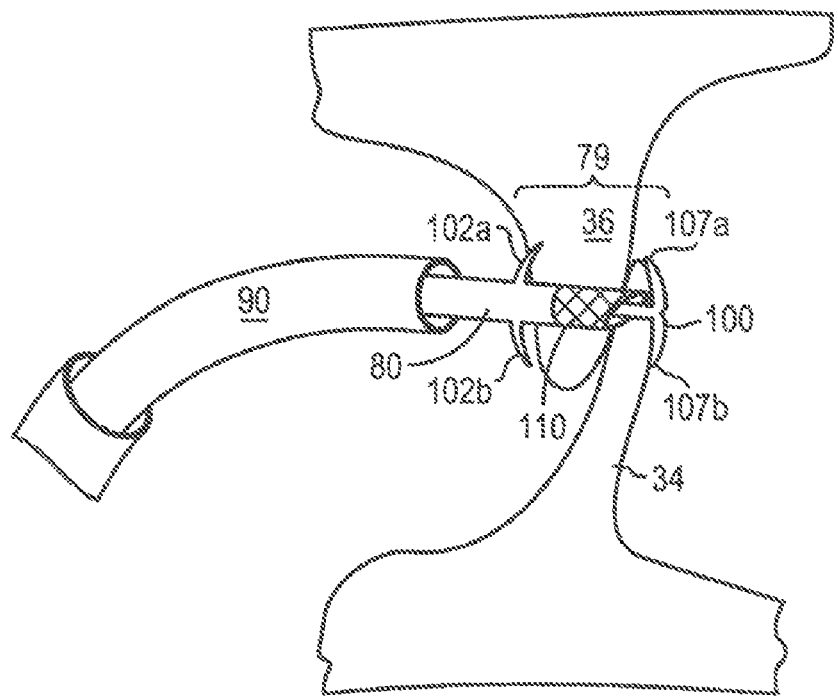
FIG. 16 is a schematic side view illustrating a step following FIG. 15 where heat is applied through a portion of the needle in the welding element, according to an illustrative embodiment of the invention.

Referring to FIG. 16, with the proximal anchor prongs 102a and 102b stabilizing the septum secundum 36, the operator pulls the distal anchor 100 in the proximal direction until it rests against the septum primum 34 or otherwise engages the septum with the prong tips 107a and 107b. As a result, the operator uses opposite forces to clamp the septa secundum 36 and primum 34 together beyond what is provided by the atrial pressure differential. In embodiments without a particular structure for proximal anchor, the operator can substitute the proximal anchor with the distal end 94 of the catheter sheath. The above steps can be similarly performed from the left atrium 30 as well, i.e., puncturing the septum primum 34 and then the septum secundum 36.

After both the proximal anchor prongs 102a and 102b, and the distal anchor 100 have been deployed to clamp the septum primum 34 and septum secundum 36 together, the operator may turn on the electrode(s) in the welding element 79 to apply heat to both the septum primum 34 and septum secundum 36. In one embodiment, the electrode is the middle section 110 of the needle 80. The needle middle section 110, in the position shown in FIG. 16, contacts both the septum primum 34 and septum secundum 36, and is not exposed to blood in the atria. In another embodiment, the electrodes are the distal anchor 100 and/or proximal anchor 127. The electrodes can be used to provide heat energy by themselves or in combination with the middle section 110 of the needle 80. Additionally, more than one puncture can be created across the septum primum 34 and the septum secundum 36 by repeating the above steps.

In another embodiment, where the proximal anchor 127 and/or distal anchor 100 is/are made of a shape-memory material, the heat created by the electrodes causes the proximal and/or distal anchor to stiffen and exert further clamping force, pushing the septum primum and septum secundum further against each other during the welding. In other words, the angle of the deployed anchors changes upon heat activation to further clamp the septum primum and septum secundum together.

After a weld is created between the septum primum 34 and septum secundum 36, the operator withdraws the distal anchor 100 into the needle 80. The operator also withdraws the proximal anchor 127 into the catheter sheath 90. Then the operator withdraws the needle 80 and the catheter sheath 90 out of the patient. The septal puncture left by the needle 80 heals over time.

Referring to FIG. 17A, in a method using an alternative embodiment where the electrode is part of the central cable 98 supporting the distal anchor 100, the distal anchor 100 is deployed and engages the septum primum 34 as described above following the step depicted in FIG. 14. The needle 80 (shown in FIG. 14) is retracted into the catheter sheath 90. Instead, to clamp the septa together, the operator uses the catheter distal end 94 to push the septum secundum 36 while pulling the septum primum 34 using the distal anchor 100. The exposed portion 112 of the central cable 98 is in contact with both septum primum 34 and septum secundum 36. Therefore, the operator can apply energy (e.g., RF) to weld the septa together.

Referring to FIGS. 17B and 17C, in an alternative embodiment, the electrode in the welding element is at least a portion of the distal anchor, e.g., its proximal surface, when deployed, that contacts the septum primum 34 and the septum secundum 36. Using the embodiment depicted in FIG. 12 as an example, the distal anchor 133 is pulled back against the septum primum 34 and the septum secundum 36 with its multiple prongs 135. The optional proximal anchor 137 may be employed to exert an opposing force in order to force the septum primum 34 against the septum secundum 36. The distal anchor 133 may be used as a single electrode that applies heat to yield several weld joints along the length of the PFO, similar to usage of interrupted sutures, or it may be used in combination with another electrode located on either the proximal anchor 137 or the middle portion 110 of the needle 80. The anchor's distal surface 139 is preferably insulated. The operator may puncture the septum primum 34 and septum secundum 36 at various locations along the PFO, and depending on the amount of electricity and heat applied, creating welds of various sizes. While the PFO may not be sealed along its entire length by a single weld, two to ten welds with relatively small intervals can be created in this fashion. These welds may not overlap at all, or overlap among some of them, or even overlap to effectively form one continuous weld. This is one approach to effectively seal off the PFO and to reduce risks of embolus resulting from blood flow from right to left atria.

Figure 18:
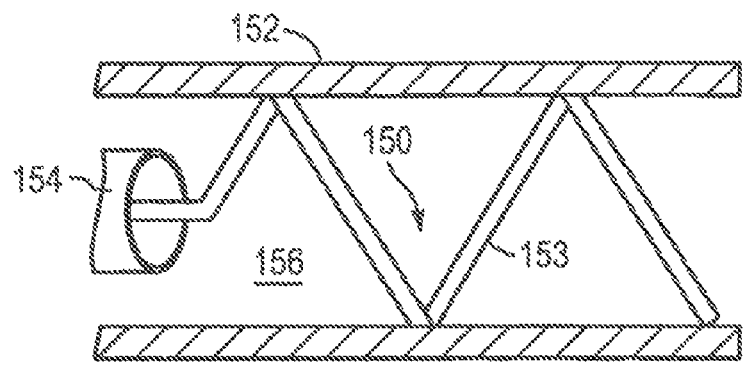
FIG. 18 is partial cross-sectional view of a catheter sheath with a side view of a coiled welding element disposed inside the sheath, according to another illustrative embodiment of the invention.
Figure 19A:
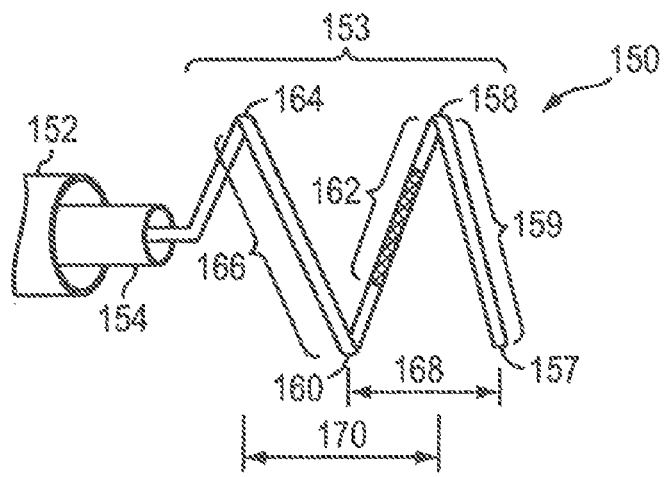
FIG. 19A is a side view of the illustrative welding element of FIG. 18 with the coil deployed, according to an illustrative embodiment of the invention.
Figure 19B:
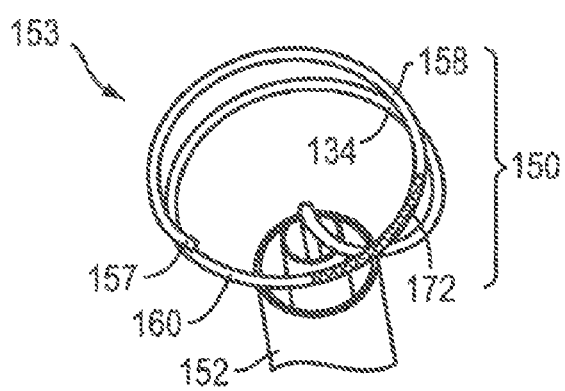
FIG. 19B is a top view of the welding element depicted in FIG. 19A.

FIGS. 18,19A and 19B depict embodiments of the invention that include a coil in the welding element. By coil, it is meant to include configurations that resemble a spiral or helix where the three-dimensional locus of a point in the configuration moves parallel to and about a central axis at a constant or varying distance. Such configurations are also commonly noted as a helix, spiral, twist, or curl. FIG. 18 depicts a cross-sectional view of a welding element 150 inside a catheter sheath 152. The welding element 150 includes a coil 153 joined to a carrying cable 154, which in turn slidingly extends inside the bore 156 of the catheter sheath 152. The coil 153 may be made of any suitable materials such as metals, alloys or plastic. In one preferred embodiment, the coil 153 is made of Nitinol.

FIGS. 19A and 19B depict, from the side and top views respectively, the deployed coil 153 outside the catheter sheath 152, e.g., when the operator twists the carrying cable 154 in one direction or simply pushes the carrying cable in the distal direction. The coil 153 typically expands in its diameter when deployed. Using a material such as Nitinol that has shape memory allows the operator to pre-select the shape and dimension of the coil 153 inside the heart, where the range of temperature is predictable. In one embodiment, the deployed coil 153 includes about one and a half turns, which can be divided into three portions in the helical structure. From a coil distal tip 157 to a half-turn point 158 down the coil is a distal section 159. From the point 158 to the next half-turn point 160 down the coil is a middle section 162. From the point 160 to the next half-turn point 164 down the coil is a proximal section 166. Of course, the coil 153 may have more or fewer turns than described by these three sections.

In the deployed state, the distance between the distal tip 157 and its corresponding point 160 one turn down the coil is a distal pitch 168. The distance between the point 158 and its corresponding point 164 one turn down the coil is a proximal pitch 170. In a preferred embodiment, the distal pitch 168 is such that at least the tip portion of a septum primum can fit between the distal tip 157 and its corresponding point 160. In other words, the distal pitch 168 is at least about 0.1 mm, and preferably less than about 4.0 mm. In a preferred embodiment, the distal pitch 168 is about 1 mm. The proximal pitch 170 is such that at least the tip portion of a septum secundum can fit between the point 158 and its corresponding point 164. In other words, the proximal pitch 170 is at least about 5 mm, and preferably between about 6 and about 20 mm.

The coil 153 may include an insulated portion and an uninsulated portion. The surface of the insulated portion does not heat up significantly when the coil 153 is energized while the uninsulated portion does. There are a variety of ways to have portions of the coil 153 differ in terms of heat conductivity. In one embodiment, the insulated portion is not connected to the source of energy and is made of a material with low heat conductivity, e.g., a polymeric material, while the uninsulated portion is connected to the energy source and made of a heat-conductive material, e.g., metal. In another embodiment, the insulated and uninsulated portions are made of essentially the same material but somehow sectionalized to be selectively heat-conductive when the coil 153 is energized. There are a variety of ways to insulate an otherwise conductive body, e.g., with a non-conductive sleeve or coating, or embedding a non-conductive barrier (not shown) between the insulated portion and the uninsulated portion. In one embodiment, a non-thrombogenic polymer half-sleeve or foam coating is applied for insulation purposes.

Still referring to FIGS. 19A and 19B, in the illustrated embodiment, an electrode 172 is the uninsulated or exposed portion of the coil middle section 162, which will contact both the septum primum and the septum secundum if they are fitted into the coil 153 as described above. Because the coil 153 is configured to position the electrode 172 to contact the target tissue, in this case, both the septa tissue, the coil 153 is a locator in that sense. In one embodiment, the coil 153 is detachable from the rest of the device, e.g., at point 164. Any conventional detachable connection can be used for this purpose, e.g., mechanical threading (not shown).

Figure 20:
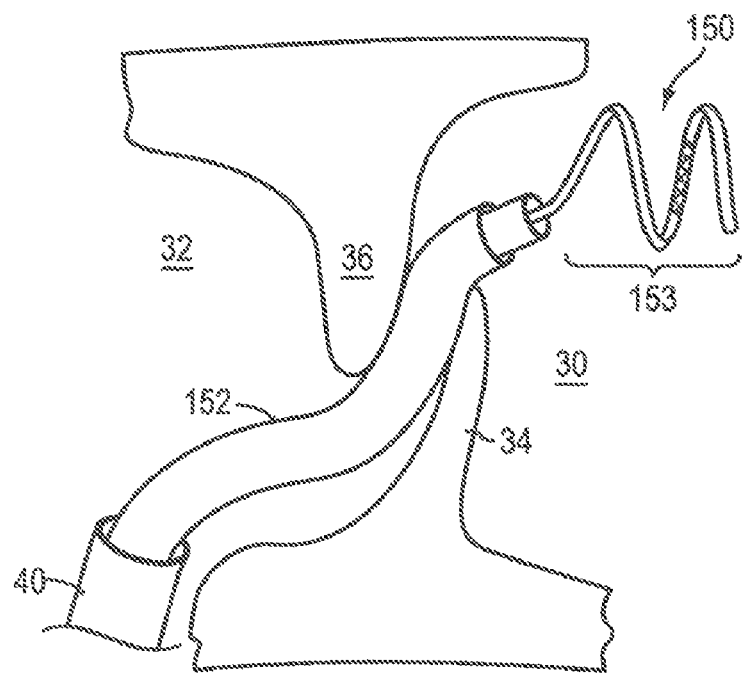
FIG. 20 is a schematic side view illustrating a PFO closure procedure using the catheter depicted in FIGS. 18, 19A, and 19B where the coil is deployed in the left atrium, according to an illustrative embodiment of the invention.
Figure 21:
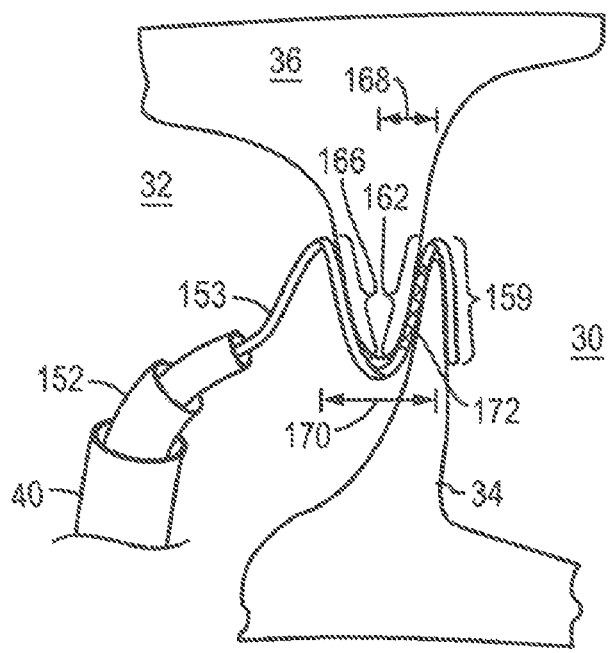
FIG. 21 is a schematic side view illustrating a step following FIG. 20 where the coil engages both the septa secundum and primum, according to an illustrative embodiment of the invention.

FIGS. 20 and 21 depict a method of using a coiled welding element for closing a PFO. Referring first to FIG. 20, the operator advances the catheter sheath 152 to the heart as described previously, e.g., through the inferior vena cava 40 to the right atrium 32, then through the PFO, to the left atrium 30. The operator then deploys the coiled welding element 150 out of the catheter sheath 152 as depicted in FIG. 20.

Referring now to FIG. 21, the operator pulls back the catheter sheath 152 and the welding element 150 until the sheath tip withdraws into the right atrium 32 and the deployed coil 153 is situated against the septum secundum 36 and the septum primum 34. The coil distal pitch 168 allows the septum primum 34 to be grasped between the distal coil section 159 and the middle coil section 162. The coil proximal pitch 170 allows the septum secundum 36 to fit between the middle coil section 162 and the proximal coil section 166. The operator may need to twist the coil 153 in order to engage the septum secundum 36 and the septum primum 34. In a preferred embodiment where the coil 153 is made of Nitinol, when the operator connects electricity, e.g., RF current, to the coil 153, the coil 153 further clamps the septum primum 34 against the septum secundum 36 as coil 153 increases in stiffness. At the same time, the exposed electrode 172 starts to heat the tissue it contacts which includes both the septum primum 34 and septum secundum 36.

After a weld is created between the septum primum 34 and septum secundum 36, the operator withdraws the welding element 150 back into the catheter sheath 152, e.g., by twisting in the counter-clock direction. Alternatively, if withdrawing the coil 153 will cause too much damage to the tissue, the operator detaches a detachable coil 153 from the rest of the welding element 150, leaving the coil 153 embedded in the tissue. Then the operator withdraws the catheter sheath 90 out of the patient.

Variations, modifications, and other implementations of what is described herein will occur to those of ordinary skill in the art without departing from the spirit and the scope of the invention. The invention is not to be defined only by the preceding illustrative description.

What is claimed is:

1. A method for treating patent foramen ovale in a patient, the method comprising:
   (a) introducing an intravascular catheter into a patient's heart, the catheter comprising a coil having an insulated distal section, an insulated proximal section, and an uninsulated middle section further comprising an electrode;
   (b) engaging the coil with both a septum secundum and a septum primum of the patent foramen ovale such that the electrode contacts both the septum secundum and septum primum; and
   (c) connecting the electrode to an energy source to heat both the septum secundum and the septum primum, and generating a clamping force in the coil to keep the septum secundum and the septum primum in contact with each other during heating.

2. The method of claim 1, wherein the insulated distal section contacts the septum primum during heating.

3. The method of claim 1, wherein the insulated proximal section contacts the septum secundum during heating.

4. The method of claim 1, wherein the uninsulated middle section comprises less that one full circumferential turn of the coil.

5. The method of claim 1, wherein the intravascular catheter further comprises an elongated sheath comprising a proximal end, a distal end, and defining a bore, wherein the coil is extendable from inside the bore.

6. The method of claim 1, wherein the coil is detachably attached to a carrying cable.

7. The method of claim 1, wherein the coil comprises a first pitch between the distal and middle sections, and a second pitch between the proximal and middle sections.

8. The method of claim 7, wherein the second pitch differs from the first pitch.

9. The method of claim 7, wherein the at least one of the first pitch or the second pitch decreases when the electrode is connected to the energy source.

10. The method of claim 7, wherein both pitches of the coil decrease when the electrode is connected to the energy source.

11. The method of claim 7, wherein the first pitch measures between about 5 mm and about 10 mm, and the second pitch measures less than about 1.5 mm.

12. The method of claim 1, wherein the coil comprises a shape memory material.

13. The method of claim 12, wherein the shape memory material is Nitinol.

14. The method of claim 1, wherein the coil is capable of releasing a welding agent to facilitate tissue reparation.

15. The method of claim 14, wherein the welding agent comprises a material selected from the group consisting of fibrinogen, collagen, and an adhesive.

16. The method of claim 1, wherein the energy source comprises a radio frequency energy source.

17. The method of claim 1, wherein the uninsulated middle section comprises a half circumferential turn of the coil.

\* \* \* \* \*